United States Patent [19]
Gelling et al.

[11] Patent Number: 6,013,816
[45] Date of Patent: Jan. 11, 2000

[54] PROCESS FOR THE PREPARATION OF A LINEAR FORMYL COMPOUND

[75] Inventors: Onko J. Gelling; Imre Toth, both of Geleen, Netherlands

[73] Assignee: DSM NV, Netherlands

[21] Appl. No.: 08/676,032

[22] Filed: Jul. 5, 1996

Related U.S. Application Data

[63] Continuation of application No. PCT/NL95/00007, Jan. 5, 1995.

[30] Foreign Application Priority Data

Jan. 7, 1994 [BE] Belgium .................. 9400017
Jan. 7, 1994 [BE] Belgium .................. 9400018

[51] Int. Cl.$^7$ ................................ C07C 227/00
[52] U.S. Cl. .................. 554/124; 554/128; 540/484; 540/485; 540/538; 558/353; 562/517; 562/523; 562/531; 562/553; 562/606; 564/469; 564/471; 564/472; 564/473; 568/448; 568/451; 568/484; 568/909

[58] Field of Search ................... 554/114, 128; 568/451, 454, 484, 904; 552/153; 540/484, 485, 538; 558/335; 562/517, 523, 531, 553, 606; 564/469, 471, 472, 473

[56] References Cited

U.S. PATENT DOCUMENTS 4,542,120  9/1985  Hsu et al. .................. 502/153
4,748,261  5/1988  Billig et al. .................. 556/404

*Primary Examiner*—Gary Geist
*Assistant Examiner*—Deborah D Carr
*Attorney, Agent, or Firm*—Pillsbury Madison & Sutro

[57] ABSTRACT

Process for the preparation of a linear ω-formyl-carboxylic acid or a corresponding linear formylnitrile compound starting from an internally unsaturated $C_4$–$C_{12}$ carboxylic acid or a corresponding ester or nitrile by means of hydroformylation in the presence of carbon monoxide, hydrogen and a catalyst system, wherein the hydroformylation is carried out in an aqueous medium and in that the catalyst system comprises platinum and a water-soluble organic bidentate ligand.

17 Claims, No Drawings

PROCESS FOR THE PREPARATION OF A LINEAR FORMYL COMPOUND

This is a continuation of PCT/NL95/00007 filed Jan. 5, 1995.

RELATED APPLICATIONS

Field of the Invention

DESCRIPTION OF THE RELATED ART

The invention relates to a process for the preparation of a linear ω-formylcarboxylic acid or a corresponding linear formylnitrile compound starting from an internally unsaturated $C_4$–$C_{12}$ carboxylic acid or a corresponding ester or nitrile by means of hydroformylation in the presence of carbon monoxide, hydrogen and a catalyst system.

Preparation of highly selective linear terminal aldehyde compounds by hydroformylation from internally unsaturated compounds is a difficult task to accomplish. The phrase internally unsaturated refers to compounds in which the unsaturated bond is not terminally situated in the chain of carbon atoms. U.S. Pat. No. 4,801,738 describes the problem of low selectivity for linear formylated products when internally unsaturated compounds are employed as precursors. That patent specification describes a process in which an internally unsaturated pentenoate ester is first isomerized to a terminally unsaturated compound (4-pentenoate ester) prior to hydroformylation with a rhodium/triphenylphosphine complex in a toluene solvent. Isomerization of the internally unsaturated compound to the terminally unsaturated compound is necessary because, otherwise, the selectivity for the terminal linear formyl compound (5-formylvalerate ester) would be undesirably low. This process is disadvantageous because of the extra isomerization step.

SUMMARY OF THE INVENTION

The object of the invention is to provide a simple process whereby an internally unsaturated carboxylic acid or a corresponding ester or nitrile can be hydroformylated to a linear formyl compound with a high degree of selectivity.

This object is achieved in that the hydroformylation is carried out in an aqueous medium and in that the catalyst system comprises platinum and a water-soluble organic bidentate ligand.

DETAILED DESCRIPTION OF THE INVENTION

It has been found that, if these linear formyl compounds are prepared using the process of the invention, the desired product can be prepared with high selectivity and in a single process step. A further advantage of this process is the high selectivity for both linear and branched aldehydes. Branched aldehydes may be useful by-products or may advantageously be converted into the starting material by means of decarbonylation. Loss of product is thus avoided by converting the (undesired) branched aldehydes into the starting material (as described in EP-A-295551 for the preparation of 5-formyl-valerate ester).

A further advantage is that the formyl carboxylic acid or the formylnitrile compound can readily be separated from the catalyst system by for example extraction with a less polar solvent than water. The catalyst system will remain in the water phase and can advantageously be reused in a next hydroformylation.

Furthermore, it can be advantageous that dicarboxylic acids are formed as by-products, when starting from the carboxylic acid or ester. The dicarboxylic acids often are useful by-products with many applications. A case in point is adipic acid, which is formed as a by-product when an internally unsaturated pentenoic acid (or pentenoate ester) is reacted according to the invention.

DESCRIPTION OF PREFERRED EMBODIMENTS

Linear, internally unsaturated $C_4$–$C_{12}$ organic nitrile compounds also can be hydroformylated according to the process invention. Examples of suitable compounds are 2-butenenitrile, 2-pentenenitrile, 3-pentenenitrile, 4-hexenenitrile, 3-hexenenitrile, 2-hexenenitrile or 9-undecanenitrile.

The carboxylic acids which can be hydroformylated with the process according to the invention contain, apart from the carboxyl group or ester group, from 4 to 12 carbon atoms. Examples of suitable internally ethylenically unsaturated carboxylic acids are 2-butenoic acid, 2- and 3-pentenoic acid, 2-, 3- and 4-hexenoic acid, 5-heptenoic acid, 5- and 6-octenoic acid, 9-undecenoic acid and polyunsaturated acids such as 2,4-hexadienoic acid and 2,4-pentadienoic acid.

The carboxylic acid ester used as starting material for the process according to the invention is generally an alkylester, an aryl ester or an aralkyl ester of for example the above mentioned carboxylic acids. The alkyl ester group may have 1 to 8 carbon atoms while, the aryl ester group or aralkyl ester group may have 6 to 12 carbon atoms. Examples of suitable ester groups are methyl, ethyl, propyl, isopropyl, n-butyl, tert-butyl, isobutyl, cyclohexyl, benzyl and phenyl ester groups. The ester group will hydrolyze during the hydroformylation and the formyl carboxylic acid will be the primary product.

Mixtures of the above-mentioned compounds can also be hydroformylated using the process of the invention. Examples of possible mixtures are mixtures of compounds in which the location of the unsaturated bond differs. Such mixtures may also contain terminally unsaturated compounds. Mixtures of carboxylic acids and carboxylic acid esters can also be hydroformylated with the process according the invention. Preferably the esters are derived from the same carboxylic acid as used as the co-reactant. Generally, the mixtures will contain at least 20% internally unsaturated compounds relative to the total of unsaturated compounds.

A preferred group of starting compounds is represented by the following formulas $$CH_3—CH=CH—CH_2—L \quad (1)$$

$$CH_3—CH_2—CH=CH—L \quad (2)$$

in which L is

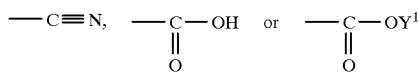

in which $Y^1$ is an alkyl group with 1 to 8 carbon atoms, an aryl group with 6 to 12 carbon atoms or an aralkyl group with 7 to 12 carbon atoms. Examples of $Y^1$ are methyl, ethyl, propyl, isopropyl, n-butyl, tert-butyl, isobutyl, cyclohexyl, benzyl and phenyl. Preferably methyl, ethyl or phenyl are used. The resulting linear aldehyde compounds obtained when starting from the compounds of formula (1) or (2) can be advantageously used in a process to make Nylon-6 or Nylon-6.6 precursors.

The advantages of the process according to the invention are the most pronounced when starting from compounds according to formula (1) or mixtures of starting compounds containing large amounts of compounds according to formula (1). This is because compounds of formula (1) or these mixtures are easy obtainable starting from butadiene. Small amounts of terminally unsaturated compounds will as a rule be present in these mixtures. For example pentenoic acid can be prepared by hydroxycarbonylating butadiene (in the presence of water and carbon monoxide) as described in EP-A-405433. A mixture of isomeric pentenoic acids is prepared, where the mixture consists primarily of 3-pentenoic acid and in small part of 4- and 2-pentenoic acid. By carbonylating butadiene with carbon monoxide and an alcohol as described in, for example, EP-A-301450, a mixture can be prepared consisting primarily of 3-pentenoate and 4- and 2-pentenoate. Pentenenitriles may be prepared by the process as described in U.S. Pat. No. 3,496,215 starting from butadiene.

Below the hydroformylation of pentenoic acid is described in particular. However, the invention is therefore not limited to this starting compound. The conditions described below will also apply to the other starting materials mentioned above.

The water-soluble compound used as the bidentate ligand may be represented by the following general formula:

$$R^1R^2—M^1—R—M^2—R^3R^4 \quad (3)$$

where $M^1$ and $M^2$ represent a phosphorus (P) atom, an antimony atom or an arsenic atom, R represents a divalent organic bridging group having at least three atoms and where $R^1$, $R^2$, $R^3$ and $R^4$ represent the same or different organic substituents, such as $C_{1-15}$ cycloalkyl or $C_5$–$C_{20}$ arly groups, preferably an aryl group, such as naphthyl, phenyl or a heterocyclic aryl group such as pyridyl, and where at least one hydrophilic group is substituted on any one of $R^1$, $R^2$, $R^3$, $R^4$ or R. It is preferred for $M^1$ and $M^2$ to be phosphorus (P) atoms.

The hydrophilic group may be any group which increases the solubility of the organic bidentate ligand in water. This hydrophilic group may be a very polar group, for example amine derivatives, such as dialkylamine groups or more preferably an ionic group. The location of the hydrophilic group in the ligand compound is not critical. The hydrophilic group may be linked to the groups $R^1$–$R^4$ or to the bridging group R.

Examples of suitable ionic hydrophilic groups are a sulphonate group, —$SO_3Z$, a phosphonate group —$PO_3Z$, a carboxylate group, —COOZ, or a cationic group of an ammonium salt —$N(R^5)_3X$, where Z represents a cationic group, $R^5$ an aliphatic or aromatic hydrocarbon group having from 1 to 18 carbon atoms or hydrogen and X represents an anionic group. If the bidentate ligand contains aryl groups, for example for any one of $R^1$, $R^2$, $R^3$ or $R^4$, the cationic group of an ammonium salt preferably is bonded to a non-aryl group in the bidentate ligand. These non-aryl groups can be the bridging group (R) or the non-aryl groups for $R^1$–$R^4$. Another example of a hydrophilic group is when a phenolate group Ar—OZ is present in the ligand. The Ar group may be any aromatic group $R^1$, $R^2$, $R^3$, $R^4$ and/or R.

Examples of suitable cationic groups (Z) are the inorganic cations of metals, especially of alkali and earth alkali metals, for example sodium, potassium, calcium and barium as well as ammonium ions or quaternary ammonium ions, for example tetramethylammonium, tetrapropylammonium or tetrabutylammonium.

Examples of suitable anionic groups (X) are halides, sulphate and phosphate groups and $R^6$—$SO_3$—, $R^6$—$CO2$— and $R^6$—$PO^3$— groups, where $R^6$ represents a $C_1$–$C_{12}$ alkyl or $C_1$–$C_{12}$ aryl.

In general, the number of hydrophilic groups is between 1 and 6, and optimally between 1 and 4 groups per molecular of bidentate ligand.

$R^1$, $R^2$, $R^3$ and $R^4$ may be $C_1$–$C_{15}$ (cyclo)alkyl groups or $C_5$–$C_{20}$ aryl groups. These groups preferably are aryl groups such as naphthyl, phenyl or a heterocyclic aryl group such as pyridyl. Examples of possible substituents are alkyl groups, for instance a methyl, ethyl or isobutyl group, alkoxy groups, for instance methoxy, ethoxy, isopropoxy and halides.

Bridging group R may be an organic group with 3–30 carbon atoms. R may be a divalent $C_9$–$C_{12}$ alkyl group, for example trimethylene, tetramethylene, pentamethylene or hexamethylene.

Examples of bidentate phosphine ligand compounds according to formula (3) without the hydrophilic group are 1,3-bis(diphenyl-phosphino)propane, 1,4-bis (diphenylphosphino)butane, 2,3-dimethyl-1,4-bis (diphenylphosphino)butane, 1,4-bis (dicyclohexylphosphino)butane, 1,3-bis(di-p-tolyl-phosphino)propane, 1,4-bis(di-p-methoxyphenylphosphino) butane, 2,3-bis(diphenylphosphino)-2-butene, 1,3-bis (diphenylphosphino)-2-oxopropane and 2-methyl-2-(methyldiphenylphosphino)-1,3-di(diphenylphosphino) propane. The above ligands, when substituted with one or more hydrophilic group, are examples of possible water-soluble bidentate ligand compounds used in the process according to the invention.

Preferably the bridging group R forms a "rigid" link between $M^1$ and $M^2$, whereby the link allows $M^1$ and $M^2$ little or no conformational freedom relative to one another, comparable to a double bond, which also allows little conformational freedom. Bidentate phosphine ligand compounds possessing a bridging group that forms non-rigid links allow more conformational freedom, yielding less favorable results. Usually, the shortest distance between $M^1$ and $M^2$ is preferably formed by 3, 4 or 5 atoms. These atoms may represent, besides carbon, a heteroatom such as the nitrogen, oxygen, sulphur and phosphor atoms.

Example of suitable "rigid" bridging groups are divalent organic groups containing at least one cyclic group in the chain between $M^1$ and $M^2$, where the cyclic group may be aromatic. This cyclic group imparts the "rigid" properties to the bridging group and may possibly be linked to $M^1$ and/or $M^2$ via an alkyl group having from 1 to 3 carbon atoms. An example of suitable bridging groups may be represented by the following general formula:

$$—R^7—Y—R^8— \qquad (4)$$

where Y represents a hydrocarbon group, which contains at least one cyclic structure. The at least one cyclic structure in parts rigidity to the bridge group, and the cyclic structure is optionally substituted the hydrocarbon group may contain heteroatoms such as oxygen, nitrogen, phosphorus and sulphur and where $R^7$ and $R^8$ may independently of one another be omitted or may independently of one another represent a $C_1$–$C_3$ alkylene group. Generally, the cyclic structure will contain from 3 to 20 atoms. $M^1$ and $M^2$ may be cis or trans to the rigid ring Y. If group $R^7$ or $R^8$ are present, individually or in combination, the group or groups too, may be cis or trans to the rigid bridge Y.

An example of a bidentate phosphine having a cyclic structure in Y which contains a heteroatom is 2,3-o-isopropylidene-2,3-dihydroxy-1,4-bis(diphenylphosphino) butane (DIOP), which is commercially available. Compounds derived from DIOP are also suitable. Another group of cyclic structures that are especially suitable for Y in formula III are cyclic alkanes such as cyclopropane, cyclobutane, cyclopentane and cyclohexane. Bridged cycloalkanes, too, are highly suitable to be used as cyclic group Y in formula III. Examples of such bridged cycloalkanes are bicyclo[1,1,2]hexane, bicyclo[2,2,1]heptane and bicyclo[2,2,2]octane.

The cyclic structure of Y may optionally be substituted with one or more aryl or alkyl groups, with or without other functional groups. The functional groups substituted on Y may also be hydrophilic groups which increase the solubility of the organic bidentate ligand used in the process according to the invention. The functional groups may optionally be used for immobilizing the bidentate phosphine on a carrier. Examples of these functional groups are, for instance, carbonyl, hydroxyl, amine and halide groups.

Other suitable "rigid" bridging groups are divalent organic groups containing at least 2 coupled, preferably aromatic, ring systems. The two ring systems have a hindered rotation relative to one another, as a result of which the bridges possess 'rigid' properties. Such compounds are described in detail in, for instance, "Advanced Organic Chemistry, Reactions, Mechanisms and Structure", Jerry March, 4th ed. 1992, John Wiley & Sons, page 101. Examples of suitable coupled ring systems are biphenyl, binaphthyl and bipyridyl. An example of a bidentate phosphine with a "rigid" bridge group with coupled ring systems is 2,2'-bis-(diphenylphosphino)-1,1'-binaphthyl (BINAP), which is commercially available. The ring systems may be substituted in the same way as the cyclic structure Y described above.

A completely different group of suitable "rigid" bridging groups R with cyclic compounds are bis(η-cyclopentadienyl)- coordination compounds of metals (also known as metallocenes). A particularly suitable metallocene is ferrocene.

Examples of suitable bidentate phosphines with rigid bridging groups (R) into which hydrophilic groups have not yet been incorporated are the earlier mentioned DIOP (A), bis(diphenylphosphine)ferrocene (B), trans-1,2-bis(di(m-methylphenyl)phosphinomethyl)cyclobutane (C), trans-[(bicyclo[2.2.1]heptane-2,3-diyl)bis(methylene)]-bis[diphenylphosphine] (D), trans-((bicyclo[2.2.2]octane-2,3-diyl)bis(methylene)]-bis[diphenylphosphine] (E), trans-1,2-bis(diphenylphosphinomethyl)cyclobutane (DPMCB) (F), trans-1,2-bis[diphenylphosphinomethyl]trans-3,4-bis[phenyl]cyclobutane (G) and the earlier mentioned BINAP. The letters in parentheses refer to the structural formulae below:

(A)

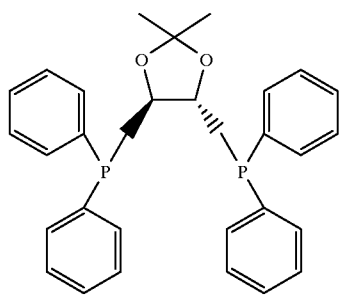

(B)

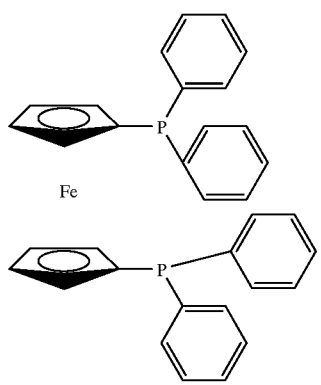

(C)

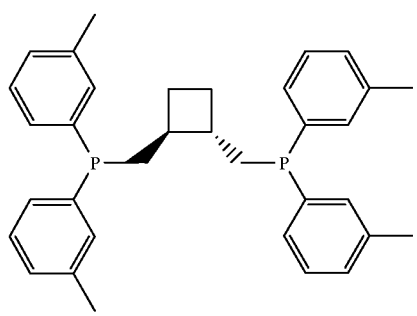

-continued

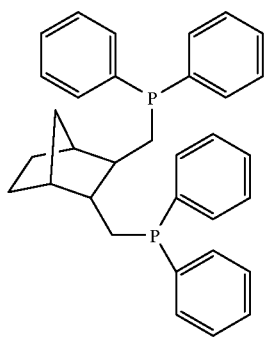

(D)

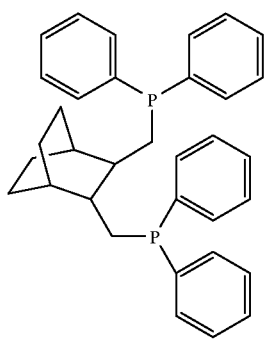

(E)

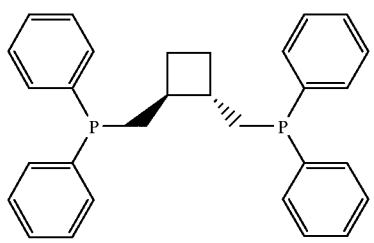

(F)

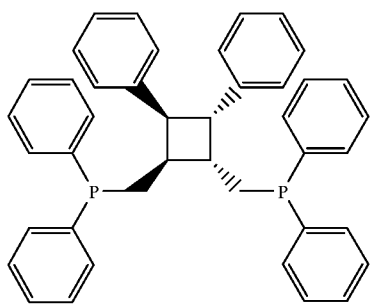

(G)

The hydrophilic groups can readily be linked to the above-mentioned compounds. Sulphonate groups, for instance, can be bonded to the ligand via sulphonation with the aid of $SO_3$ in sulphuric acid. Carboxylate groups, phosphonate groups and cationic radicals of an ammonium salt can be incorporated using synthesis processes known in the art.

Promotors are preferably added to the catalyst system to further improve the selectivity to linear products. These promotors are acids with an pKa<2 (measured at 18° C. in an aqueous solution), preferably sulphonic acids, for example sulphonic acid, trifluoromethane sulphonic acid, tert-butyl sulphonic acid or p-toluene sulphonic acid. The molar ratio of acid to platinum may be between 1:1 and 30:1 and preferably between 1:1 and 10:1.

Platinum or the platinum compound can be applied in a homogeneous system or a heterogeneous, immobilized system. Homogeneous systems are preferred. Since platinum forms a complex with the bidentate compound in situ, the choice of an initial Pt compound is not generally critical. Suitable platinum compounds are, for example salts of platinum with, for instance, hydrogen halides, nitric acid, sulphonic acid and carboxylic acids having not more than 12 carbon atoms per molecule. Examples of such salts are $PtCl_2$, $Pt(AcAc)_2$ (AcAc=acetylacetonate), $CODPtCl_2$ (COD=cyclooctadiene), $Pt(CH_3CN)_4(BF_4)_2$ and $CODPt(AcAc)BF_4$.

The aqueous medium is normally water. Although other solvents may optionally be present. Examples of other solvents are dimethyl formamide, tetrahydrofuran, benzonitril and acetonitril.

The temperature of the hydroformylation is generally between 50° and 200° C. and preferably between 90° and 120° C.

The pressure is not critical and may, for example, be between 4 and 20 MPa.

The molar ratio of hydrogen to carbon monoxide may, for example, be between 1:10 and 10:1. This ratio affects the ratio of the yield of formyl carboxylic acids to the yield of dicarboxylic acids. The dicarboxylic acids content of the resulting reaction mixture will increase as more carbon monoxide is used. If the desired product is formyl carboxylic acid, the molar ratio of carbon monoxide to hydrogen will be about 1:1. If a significant amount of dicarboxylic acids is desired, the molar excess of carbon monoxide relative to hydrogen is higher than 5.

The molar ratio of unsaturated carboxylic acid to platinum as a rule is between 100:1 and 1000:1 but is preferably between 400:1 and 600:1.

The molar ratio of unsaturated carboxylic acid and water generally lies between 1:20 and 1:2.

The hydroformylation is preferably performed continuously. The process of the invention can advantageously be conducted in a manner wherein the hydroformylation takes place in a first step (a reaction zone), followed by a second step in which the catalyst is separated from the product. Examples of possible reaction zones are one or more continuously stirred tank reactors or a tubular reactor. Since the catalyst readily dissolves in the water phase, the formyl carboxylic acids can easily be separated from the catalyst-containing water phase. Possible separation techniques are, for example, distillation, crystallization and extraction. The reaction products are preferably isolated from the water phase by means of extraction with a less polar organic solvent. Possible organic solvents are, for instance, aromatic solvents such as benzene, toluene, xylene and ethers, for example diethylether, methyl t-butyl ether, esters, for example butylacetate, ethylacetate and other solvents, for example dichloromethane, 1,2-dichloroethane, dioxane, diglyme. After the products have been separated from the water phase, the catalyst-containing water phase may advantageously be recirculated to the reaction zone. An advantage of the catalyst system according to the invention is that little or no platinum and ligand are lost when the products are extracted by the organic extraction agent.

The linear formyl carboxylic acid or the linear formylnitrile can be separated from the other by-products, for example the non-linear aldehyde by-products, by normal separation techniques, such as crystallization, extraction or distillation, for example extractive distillation.

The invention also relates to a process for the preparation of terminal dicarboxylic acids in general and of adipic acid in particular starting from terminal ω-formylcarboxylic acid and 5-formylvaleric acid respectively, in which the starting compounds are obtained by the above described process. The yield of dicarboxylic acids prepared by the aforementioned process will in this process be increased by oxidizing the formyl carboxylic acid formed, preferably in the presence of the already formed dicarboxylic acids. Such oxidation is described in, for instance, EP-A-295551, EP-A-131860 and in Basic Principles of Organic Chemistry (J. D. Roberts, M. C. Caserio, 2nd ed., pp 712–713). Generally, the formyl carboxylic acid is oxidized at 50° to 80° C. in the presence of oxygen or an oxygen-containing gas, optionally in the presence of a catalyst. That catalyst may be for instance an Mn or Co-containing catalyst.

The invention in addition relates to a process for the preparation of terminal aminocarboxylic acid and especially 6-aminocaproic acid. For example the 5-formylvaleric acid prepared by the process according to the invention can advantageously be converted into 6-aminocaproic acid by reductive amination with hydrogen and ammonia. The reductive amination of the 5-formyl valeric acid can be effected using the process described in, for instance, U.S. Pat. No. 4,950,429. Usually, the reductive amination is effected with an excess of ammonia and hydrogen in the presence of a hydrogenation catalyst and optionally a solvent at a temperature of from 50° to 150° C. and at increased pressure of from 1.0 to 40 MPa. Examples of suitable solvents are water and mono or polyhydric alcohols having from 1 to 5 carbon atoms. Water is the preferred solvent of choice.

Examples of suitable hydrogenation catalysts are metals from Group VIII of the Periodic System of Elements (CAS version, from Chemical and Engineering News, 63(5), 27, 1985). Examples of such catalysts are cobalt and nickel catalysts and the noble-metal catalysts ruthenium, platinum and palladium. The catalysts may contain activity-enhancing additives. Examples of such additives are Zr, Mn, Cu and Cr. The catalysts may consist in their entirety of the above-mentioned elements or of a carrier, for instance aluminium oxide, kiesel gel, activated carbon, carrying the active metals. For more information on how the reductive amination should be conducted, reference is for brevity made to the aforementioned U.S. Pat. No. 4,950,429.

6-aminocaproic acid prepared by the above described process starting from 5-formylvaleric acid can advantageously be converted into ε-caprolactam by means of ring closure at 150°–370° C. in a suitable solvent, for example an $C_1$–$C_6$ alkanol or water.

With the above described process for preparing ε-caprolactam it is possible to diminish the number of process steps compared to the prior art, such as the process described in U.S. Pat. No. 4,950,429. This patent describes a process in which a 5-formylvalerate ester, obtained by hydroformylation, is first saponified to 5-formylvaleric acid, then converted to 6-aminocaproic acid by means of reductive amination and subsequently the 6-aminocaproic acid is cyclisized to ε-caprolactam. With the process according to the invention it is possible to directly start the reductive amination with the product of the hydroformylation without an additional saponification step.

The following non-limiting examples further describe the invention. The selectivity mentioned in the examples is calculated as the molar amount of the specific product formed relative to the molar amount of substrate converted times 100%.

EXAMPLE I

The following were weighed into a 150-ml Hastalloy C autoclave: 37.4 mg (0.1 mmol) of $CODPtCl_2$ (COD=1,5-cyclooctadiene) and 89.7 mg (0.1 mmol) of tetrasulphonated trans-1,2-bis(diphenylphosphinomethylene)cyclobutane in 45 ml of degassed water. After half an hour of stirring, 4.9 g of freshly distilled 3-pentenoic acid was added and the autoclave was heated to 100° C. at 5.0 MPa with $CO/H_2=1$ (mol/mol). The final pressure was adjusted to 8.0 MPa with the $CO/H_2$ gas mixture. After 4 hours the reaction mixture was cooled, depressurized and the aqueous mixture was extracted with 3×100 ml of diethyl ether. The etheral phases were collected and the residual aqueous phase was evaporated at 50° C., 50 mm Hg. Next, 200 ml of toluene and 1.0 g of decane was added. This organic layer was analyzed by gas chromatography (GC). The water phase was evaporated until a solid residue remained. The obtained residue was dissolved in diethylether and after adding 0.2 g of decane the solution was analyzed by GC. This brought the overall mass balance to 94.1%, the conversion was 80.3%, the selectivity for aldehydes was 83%, N/Br (N/Br=linear aldehyde/branched aldehyde)=3.4, the selectivity for valeric acid was 4.6%, the selectivity for adipic acid was 8.1%.

EXAMPLE II

Example I was repeated except that the tetrasulphonated trans-1,2-bis(diphenylphosphinomethylene)cyclobutane was replaced by monosulphonated trans-1,2-(diphenylphosphinomethylene)cyclobutane. The conversion was 23.5%. The selectivity for aldehydes was 94.6%, N/Br= 5.25, while the selectivity for valeric acid was 4.9%. No dicarboxylic acids were formed.

EXAMPLE III

Example I was repeated except that 2-pentenoic acid was used in place of 3-pentenoic acid.

After 3 hours of reaction time, the conversion was 37.1%, the selectivity for aldehydes was 84.2%, N/Br was 3.5, the selectivity for valeric acid was 5.7% and the selectivity for dicarboxylic acids was 9.4%.

EXAMPLE IV

Example I was repeated except with that 30 ml of degassed toluene and 17.5 µl (0.2 mmol) trifluoromethanesulphuric acid were added to the aqueous mixture, before the addition of the substrate in the process of Example I. After 3.5 hours of reaction time a conversion of 86% was reached. The selectivity for aldehydes was 86.9% with N/Br of 3.9.

The selectivity for valeric acid and dicarboxylic acids was 5.2% and 7.2%, respectively.

EXAMPLE V

Example I was repeated except with that, one half of the amounts of CODPtCl$_2$ and the phosphine ligand of Example I were used and the reaction was carried out at 130° C. under 100 bar of CO/H$_2$=1/1. After 1 hour of reaction time the conversion was 68%, the selectivity to aldehydes was 71.8% with N/Br of 3.0. The selectivity to valeric acid and dicarboxylic acid was 16.8% and 11.2%, respectively.

EXAMPLE VI

Example I was repeated except that, 58.4 mg (0.1 mmol) of trans-1.2-bis[phenyl-(4-lithiumsulfonato-1-butyl) phosphinomethylene]cyclobutane was used instead of the tetrasulphonated phosphine. After 5 hours of reaction time a conversion of 35.2% was reached. The selectivity to aldehydes was 90.7% with a N/Br of 2.6. The selectivity to valeric acid was 9.3%. No dicarboxylic acid products were obtained.

EXAMPLE VII

Example I was repeated except with that, 41.1 mg (0.1 mmol) Pt(COD)$_2$ was used instead of CODPtCl$_2$ and 30 ml of degassed toluene was added before the addition of the substrate. After 4 hours of reaction time a conversion of 72.5% was reached. The selectivity for aldehydes was 86.5% with a N/Br of 4.0. The selectivity for valeric acid and dicarboxylic acids was 4.5% and 9.0%, respectively.

EXAMPLE VIII

Example I was repeated using 5.3 g of 3-pentenoic acid. The pressure was relieved after the reaction mixture had cooled down. The aqueous reaction mixture was then extracted with ether (3×50 ml) under a nitrogen atmosphere. After this first cycle the ether phase was analyzed by GC. The amounts of products and starting materials in the ether layer are given in Table 1. Hereafter, an amount of fresh 3-pentenoic acid was added to the aqueous phase (Table 1, column 1), whereupon the reaction was repeated in the manner described above. This cycle was repeated five times. The etheral extract was analyzed by GC after each cycle. After the last cycle the water phase was also analyzed by GC. Table 1 shows the amounts of 3-pentenoic acid and the results of each cycle. These results indicate that the catalyst can readily be reused while retaining its activity.

The total conversion after 4 cycles was 78.8%. The selectivity for valeric acid was 6.2%, for 5-formylvaleric acid 62%, for total formylvaleric acids 80.3%, for dicarboxylic acids 11.4%. N/Br was 3.4.

EXAMPLE IX

To purify 5-formylvaleric acid (5 FVA) by crystallisation: 3.0 g mixture of 5-formylvaleric acid (80%), 4-formylvaleric acid (16%) and 3-formylvaleric acid (4%), obtained by the process according to the invention, was dissolved in methyl tert-butyl ether at room temperature. Upon cooling at −20° C., 1.4 g of a white crystalline material was obtained, with a melting point 36°–37° C. According to $^1$H NMR and GC analysis this material consisted of more than 96% of 5-formylvaleric acid.

EXAMPLE X

The following were weighed into a 150-ml hastalloy C autoclave: 37.4 mg of CODPtCL$_2$ (COD=1,5-cyclooctadiene) and 90 mg of tetra sulphonated trans-1,2-bis(diphenylphosphino-methylene)cyclobutane in 45 ml of degassed water. After half an hour, 4.43 g of trans-3-pentenenitrile was added and the autoclave was heated to 100° C. at 5.0 MPa with CO/H$_2$=1. The final pressure was adjusted to 8.0 MPa with the same CO/H$_2$ mixture. After 4 hours the reaction mixture was cooled and the water layer was extracted 3 times using 100 ml of diethylether. Next, anisole was added to the ether layer as internal standard. The molar mass of all components was determined by GC-MS. Also, a portion of the ether layer was concentrated by evaporation and analyzed by $^1$H and $^{13}$C NMR, generating the following results: conversion was 20.7%. total aldehyde selectivity was 91.4 wt.% (N/Br=6.6; N/Br=linear aldehyde/branched aldehyde). The selectivity for to pentenenitrile was 3.7 wt.% and for carboxylic acid nitrile compounds was 3.0 wt. %. Practically no isomerization to trans-2-pentenenitrile was observed.

TABLE 1

| 3-PA added (g) (1) | cycle | PA-s (g) (2) | VA (gPa) (3) | 5-FVA (gPa) (4) | FVA (gPa) (5) | dicarboxylic acids (gPa) (6) | rest (gPa) | total (gPa) | ToF (7) |
|---|---|---|---|---|---|---|---|---|---|
| 5.30 | 1 | 1.16 | 0.25 | 1.85 | 2.51 | Π0.34 | 0.04 | 4.30 | 103.3 |
| 4.84 | 2 | 0,70 | 0,25 | 2.38 | 3.11 | 0.51 | 0.05 | 4.62 | 103.3 |
| 4.97 | 3 | 0,76 | 0,26 | 2.72 | 3.52 | 0.52 | 0.10 | 5.17 | 105.0 |
| 5.97 | 4 (8a) | 1,85 | 0,26 | 2.83 | 3.63 | 0.50 | 0.12 | 6.36 | 103.0 |
|  | (8b) | 0,01 | — | 0.52 | 0.56 | 0.02 | 0.02 | 0.61 |  |
| 21.08 (9) |  | 4,47 | 1,02 | 10.29 | 13.34 | 1.89 | 0.33 | 21.05 |  |
| results after 4 cycles |  | conv. (%) | sel$_{VA}$ (10) | sel$_{5-FVA}$ | sel$_{FVA}$ | sel$_{dicarboxylic\ acids}$ | sel$_{rest}$ | mass balance | ToF |
|  |  | 78.8 | 6.1 | 62.0 | 80.3 | 11.4 N/Br = 1.9 | 2.1 | 99.9 | 104 |

(1): amount of 3-PA (3-pentenoic acid) added;
(2): amount of pentenoic acid (PA) in ether layer;

TABLE 1-continued

| 3-PA added (g) (1) | cycle | PA-s (g) (2) | VA (gPa) (3) | 5-FVA (gPa) (4) | FVA (gPa) (5) | dicarboxylic acids (gPa) (6) | rest (gPa) | total (gPa) | ToF (7) |
|---|---|---|---|---|---|---|---|---|---|

(3): amount of valeric acid (VA) in ether layer expressed in grammes of 3-pentenoic acid (gPa);
(4): ditto for 5-formylvaleric acid (5-FVA);
(5): ditto for total of isomeric formylvaleric acids (FVA);
(6): ditto for dicarboxylic acids;
(7): ToF = turn-over frequency = moles of product prepared per mole of platinum per hour;
(8a): composition of ether phase;
(8b): composition of water phase;
(9): results of the total after 4 cycles;
(10): total selectivity (sel) for valeric acid, 5-formylvaleric acid etc. after 4 cycles

What we claim is:

1. A process for hydroformylating an internally unsaturated $C_4$–$C_{12}$ carboxylic acid, a corresponding ester, or a corresponding nitrile to produce a linear ω-formyl-carboxylic acid or a corresponding linear formyl nitrile compound, wherein said process is carried out under effective hydroformylation conditions in an aqueous medium in the presence of carbon monoxide, hydrogen, and a catalyst comprising platinum and a water-soluble organic bidentate ligand.

2. The process according to claim 1, wherein the water-soluble bidentate ligand is represented by the following general formula: $R^1R^2$—$M^1$—R—$M^2$—$R^3R^4$, where $M^1$ and $M^2$ represent a phosphorous (P) atom, an antimony atom or an arsenic atom, R represents a divalent organic bridging group having at least three atoms, and wherein $R^1$, $R^2$, $R^3$ and $R^4$ are independently $C_1$–$C_{15}$ alkyl, $C_3$–$C_{15}$ cycloalkyl or $C_5$–$C_{20}$ aryl groups and where at least one hydrophilic group is substituted on at least one of the groups $R^1$, $R^2$, $R^3$, $R^4$ or R.

3. The process according to claim 2, wherein the aryl group is selected from the group consisting of naphthyl and phenyl.

4. The process according to claim 2, wherein the aryl group is a heterocyclic group.

5. The process according to claim 2, wherein the bridging group R contains 3–30 carbon atoms.

6. The process according to claim 2, wherein the bridging group R is selected from the class of divalent $C_9$–$C_{12}$ alkyl groups.

7. The process according to claim 2, wherein the bridging group R forms a rigid link between $M^1$ and $M^2$.

8. The process according to claim 2, wherein $M^1$ and $M^2$ represent a phosphorous atom.

9. The process according to claim 2, wherein the bridging group R forms a rigid link between $M^1$ and $M^2$, and wherein $M^1$ and $M^2$ represent a phosphorous atom.

10. The process according to claim 2, wherein the hydrophilic group is a sulphonate group (—$SO_3Z$), a phosphonate group (—$PO_3Z$), a carboxylate group (—COOZ), or a cationic group of an ammonium salt (—$N(R^5)_3X$), wherein Z represents a cationic group, $R^5$ represents an aliphatic hydrocarbon group having from 1 to 18 carbon atoms and X represents an anionic group.

11. The process according to claim 7 or claim 8, wherein the hydrophilic group is a sulphonate group (—$SO_3Z$), a phosphonate group (—$PO_3Z$), a carboxylate group (—COOZ), or a cationic group of an ammonium salt (—$N(R^5)_3X$), wherein Z represents an aliphatic hydrocarbon group having from 1 to 18 carbon atoms and X represents an anionic group.

12. The process according to claim 1 for the preparation of a linear ω-formyl-carboxylic acid or a corresponding linear formyl-nitrile compound, wherein an acid with a pKa<2 is included in the hydroformylating reaction.

13. The process according to claim 1, wherein said internally unsaturated carboxylic acid or ester or nitrile is represented by at least one of the following formulas:

   (1)

   (2)

wherein L is

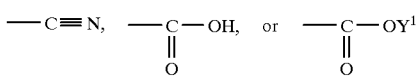

wherein $Y^1$ represents an alkyl group with 1 to 8 carbon atoms, an aryl group with 6 to 12 carbon atoms or an aralkyl group with 7 to 12 carbon atoms.

14. The process for preparing a linear ω-formyl-carboxylic acid according to claim 1, 2, 7, 8, 9, 10, 12 or 13, wherein the process further comprises after the hydroformylating, separating the ω-formyl-carboxylic acid from the catalyst-containing aqueous hydroformylation mixture by means of extraction, and returning the resulting aqueous mixture, containing the catalyst system to the hydroformylating step.

15. A process for preparing 6-aminocaproic acid via reductive amination of 5-formylvaleric acid, wherein the 5-formylvaleric acid is obtained by the process according to claim 14.

16. The process for preparing ε-caprolactam from 6-aminocaproic acid obtained by the process according to claim 15, in which process 6-aminocaproic acid is converted into ε-caprolactam via ring closure at 150°–370° C. in a solvent.

17. The process for the conversion of 5-formylvaleric acid to adipic acid comprising the combination of steps of providing a mixture of adipic acid and 5-formylvaleric acid obtained according to the process according to claim 13; and oxidizing the 5-formylvaleric acid to adipic acid.

* * * * *